United States Patent [19]

Kaeding

[11] 4,104,319
[45] Aug. 1, 1978

[54] ETHYLATION OF MONO ALKYL BENZENE

[75] Inventor: Warren W. Kaeding, Westfield, N.J.

[73] Assignee: Mobil Oil Corporation, New York, N.Y.

[21] Appl. No.: 809,510

[22] Filed: Jun. 23, 1977

[51] Int. Cl.² .................................................. C07C 3/52
[52] U.S. Cl. .............................. 260/671 C; 260/671 R
[58] Field of Search ....................... 260/671 R, 671 C; 252/455 Z

[56] References Cited

U.S. PATENT DOCUMENTS 3,751,506  8/1973  Burress ............................. 260/671 C
3,941,871  3/1976  Dwyer et al. ........................ 423/328

Primary Examiner—Delbert E. Gantz
Assistant Examiner—C. E. Spresser
Attorney, Agent, or Firm—Charles A. Huggett; Raymond W. Barclay

[57] ABSTRACT

A catalytic process is provided for the ethylation of a mono alkyl benzene wherein the alkyl group contains 1 or 2 carbon atoms, i.e. toluene or ethylbenzene to yield a mixture of ethyl toluene or diethylbenzene isomers with minimal undesired by-product formation which comprises contacting said mono alkyl benzene under conversion conditions, with an ethylating agent in the presence of a catalyst comprising a crystalline aluminosilicate zeolite characterized by a constraint index, as hereinafter defined, within the approximate range of 1 to 12 and a silica to alumina ratio greater than about 500.

12 Claims, No Drawings

ETHYLATION OF MONO ALKYL BENZENE

BACKGROUND OF THE INVENTION

1. Field of the Invention

This invention relates to a process for producing ethyl toluene or diethylbenzene with minimal undesired by-product formation utilizing a specified crystalline aluminosilicate zeolite catalyst.

2. Description of the Prior Art

Alkylation of aromatic hydrocarbons utilizing crystalline aluminosilicate catalysts has heretofore been described. U.S. Pat. No. 2,904,679 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g. benzene with ethylene, in the presence of a ZSM-5 type zeolite catalyst.

While the above-noted prior art is considered of interest in connection with the subject matter of the present invention, the toluene ethylation process described herein in which undesired by-products, including light gases such as methane, ethane, propane, propylene and $C_4$ olefins and $C_4$ paraffins and unwanted aromatics such as benzene, ethylbenzene and xylenes are minimized utilizing a catalyst of a crystalline aluminosilicate zeolite having a constraint index of 1 to 12 and a silica/alumina ratio in excess of about 500 has not, insofar as is known, been heretofore described.

Ethyltoluene and diethylbenzene are valuable chemicals. They are also subject to dehydrogenation to produce vinyltoluene and divinylbenzene respectively. It is evident that the presence of substantial quantities of unwanted light gases or other aromatics in the ethyltoluene or diethylbenzene product of interest is highly undesirable. Some of the unwanted by-products, particularly those of aromatic configuration, have been difficult to separate from the desired ethyl-substituted product. It has accordingly heretofore been necessary to remove these unwanted by-products from the desired ethyltoluene or diethylbenzene product by expensive distillation techniques, especially in instances where said product is intended for subsequent dehydrogenation.

It is evident that the availability of ethyltoluene or diethylbenzene in which interfering by-products are absent or at least present in minimum amount would eliminate the necessity for expensive prior removal of such products.

SUMMARY OF THE INVENTION

In accordance with the present invention, a process has been discovered for producing ethyltoluene or diethylbenzene containing minimal amounts of undesired by-products, thus eliminating the heretofore necessary expensive purification procedures and loss of starting materials to undesired products. Following the teachings of this invention, ethyltoluene and diethylbenzene may be produced with only trace amount of unwanted other aromatics and light gaseous by-products.

The process of the invention involves ethylation of a mono alkyl benzene wherein the alkyl substituent contains 1 or 2 carbon atoms by contacting said mono alkyl benzene with an ethylating agent, under conversion conditions, in the presence of a catalyst comprising a crystalline aluminosilicate zeolite characterized by a constraint index within the approximate range of 1 to 12 and a silica/alumina ratio greater than about 500. It has been found that the latter silica/alumina ratio is a critical parameter in achieving low production of unwanted by-products during the ethylation reaction. Crystalline aluminosilicate zeolite catalysts heretofore employed in alkylation of aromatics have been characterized by a silica/alumina mole ratio of 300 or less. Generally, such ratio has not exceeded about 100. The use of these type crystalline aluminosilicate zeolite catalysts has led to the formation of considerable amounts of the aforementioned undesired by-products, particularly under conditions of high temperature.

Ethylation, in accordance with the process described herein, is effectively accomplished at a temperature between about 250° and about 600° C., at a pressure of between about 0.1 and about 100 atmospheres utilizing a feed weight hourly space velocity (WHSV) between about 0.1 and about 100. The latter WHSV is based upon the weight of catalyst composition, i.e. total weight of active catalyst and binder therefore. The molar feed ratio of toluene/ethylating agent is generally between about 1 and about 10.

DESCRIPTION OF SPECIFIC EMBODIMENTS

The ethylating agent employed for effecting ethylation of toluene or ethylbenzene in accordance with the present invention is generally ethylene or a gaseous mixture high in this reactant. The latter may comprise refinery streams or other gaseous product mixtures of high ethylene content. Other suitable ethylating agents include ethyl alcohol and ethyl halides, e.g. ethyl chloride; diethyl ether, diethyl sulfide and ethylmercaptan.

In accordance with the present invention, the above-described reactants are brought into contact, under conversion conditions, with a bed comprising particle form catalyst containing a crystalline aluminosilicate having a constraint index within the approximate range of 1 to 12 and a silica/alumina mole ratio greater than about 500 and as high as 2000.

The zeolite catalysts utilized herein are members of a novel class of zeolites exhibiting some unusual properties. The zeolites induce profound transformation of aliphatic hydrocarbons to aromatic hydrocarbons in commercially desirable yields and are generally highly effective in conversion reactions involving aromatic hydrocarbons. Although they have usually low alumina contents, i.e. high silica to alumina ratios, they are very active even when the silica to alumina ratio exceeds 30. The activity is surprising since catalyst activity is generally attributed to framework aluminum atoms and cations associated with these aluminum atoms. This is especially surprising in the present instance since high activity was observed even with a silica/alumina ratio of 1600/1. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 500 and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 500 are useful, it is preferred to use zeolites having higher ratios of at least about 1000. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° and 950° F. to give an overall conversion between 10% and 60%. The mixture of hydrocarbons is passed at 1 liquid hourly spaced velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes. However, in all instances, at a temperature within the above-specified range of 550° to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. Application Ser. No. 528,060, filed Nov. 29, 1974. This zeolite can be identified, in terms of mole ratios of oxides and in the anhydrous state, as follows:

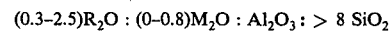

$(0.3-2.5)R_2O : (0-0.8)M_2O : Al_2O_3 : > 8 SiO_2$ wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0-0.6)M_2O : Al_2O_3 : xSiO_2$$

wherein R is an organic nitrogen-containing cation derived from a 2-hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33Å.

TABLE I

| d (Å) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° C. for a period of time of from about 6 hours to about 100 days. A more preferred temperature range is from about 150° to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8 SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

$$(0.4-2.5)R_2O : (0.0.6)M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33Å. Close examination of some individual samples of ZSM-35 may show a very weak line at 11.3–11.5Å. This very weak line, however, is determined not to be a significant line for ZSM-35.

TABLE II

| d (Å) | I/Io |
|---|---|
| 9.6 ± 0.2— | Very Strong–Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |

TABLE II-continued

| d (Å) | I/Io |
|---|---|
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane ZSM-35 (after calcination at 600° C.) is less than 10, whereas the ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° C. for a period of time of from about 6 hours to about 100 days. A more preferred temperature range is from about 150° to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 500 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The zeolites employed herein may also be physically mixed or diluted with particle-form solid of either an appropriate catalytic nature or substantially devoid of catalytic activity. Typical of the latter are silica particles such as low surface area quartz chips.

The conversion process described herein may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g. air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5-2%) is used to burn the coke in a controlled manner so as to limit the temperature to a maximum of around 500°-550° C.

The following examples will serve to illustrate the process of the invention without limiting the same:

EXAMPLE 1

ZSM-5 characterized by a high silica/alumina mole ratio was prepared as follows:

I — PREREACTED ORGANICS PREPARATION

The following materials were charged to a 30 gallon autoclave; 16,524 grams of methylethyl ketone, 10,008 grams of tri-n-propylamine and 8604 grams of n-propyl bromide. The contents were mixed with gentle agitation for 15 minutes. The agitation was stopped and 123 lbs. of water were charged to the autoclave. The autoclave was sealed and heated to 220° F and held at 220° F for 15 hours. After this reaction period, the temperature was raised to 320° F and the unreacted organics were flashed off. The aqueous phase was removed containing the prereacted organics and contained 1.44% wt. nitrogen.

II — ZEOLITE SYNTHESIS (a) Solution Preparation

Silicate Solution
  90.9 lb: Q-brand sodium silicate
  52.6 lb: $H_2O$
  118 g: Daxad 27 (sodium salt of polymerized substituted benzenoid alkyl sulfonic acid combined with a suspending agent)
Acid Solution
  4138 g. $H_2SO_4$
  1840 g. NaCl
  50.7 g. Prereacted organics
  14.7 lb. $H_2O$
Additional Solids
  5890 g. NaCl
Additional Liquid
  1180 g. $H_2O$ (b) Procedure The silicate solution and acid solution were mixed in a mixing nozzle to form a gel which was discharged into a 30 gallon autoclave to which 1180 grams of water had been previously added. The gel was whipped by agitation and 5890 grams of NaCl were added and thoroughly blended. The autoclave was sealed and heated to ~220° F with agitation at 90 rpm and held for 54.3 hours until crystallization was completed. The contents of the autoclave were cooled and discharged. The crystallized product was analyzed by x-ray diffraction and was found to be 100% wt. ZSM-5. The chemical analysis of the thoroughly washed crystalline product was:

|        | % Wt. | Mole Ratio |
|--------|-------|------------|
| $Al_2O_3$ | 0.10  | 1.0        |
| $SiO_2$   | 98.3  | 1670       |
| Na        | 1.6   | —          |
| $Na_2O$   | —     | 35.5       |
| N         | 0.75  | 63.9       |
| C         | 8.98  | 892        |

EXAMPLE 2

ZSM-5 having a silica/alumina mole ratio of about 70 was prepared as follows:

1874 pounds of tri-n-propylamine were mixed with 1610 lbs of n-propyl bromide, 3100 pounds of methyl ethyl ketone and 1254 gallons of deionized water. The mixture was reacted at 210°-218° F, 5 RPM for 14 hours in an autoclave equipped with high shear agitation. The resulting aqueous phase was designated Solution A.

586 gallons of deionized water were mixed with enough Q-brand sodium silicate to give a solution with a specific gravity of 1.222. 24 pounds of Daxad 27 were added to the solution. The resulting solution was designated Solution B.

305 pounds of commercial grade aluminum sulfate (17.2% $Al_2O_3$) were dissolved in 437 gallons of deionized water. To this solution, 733 pounds of sulfuric acid (93.2 wt. % $H_2SO_4$), 377 pounds of commercial grade NaCl and 1915 pounds of Solution A were added. The resulting solution was designated Solution C.

20 gallons of deionized water were added to an autoclave equipped with high shear agitation. Solution B and Solution C were mixed simultaneously in a nozzle and sprayed into the autoclave. 1200 pounds of commercial grade NaCl were added to the autoclave. The resulting gel was mixed in the autoclave at 90 rpm and ambient temperature for 4 hours. The gel was then reacted at 206°–226° F and 90 rpm for 40 hours and at 320° F and 90 rpm for 3 hours. The solid product was analyzed by x-ray diffraction and found to be ZSM-5. The solid product was washed by decantation with deionized water and 3500 ppm Primafloc C-7 (polyammonium bisulfate) until the sodium content of the product was less than 1%. The solid product was filtered on a rotary drum filter. The resulting filter cake was dried at 310° F.

The chemical analysis of the dried product was:

|  | % Wt. | Mole Ratio |
|---|---|---|
| $Al_2O_3$ | 2.39 | 1.0 |
| $SiO_2$ | 97.0 | 68.9 |
| Na | 0.96 | — |
| $Na_2O$ | — | .89 |
| N | 0.85 | 2.59 |
| C | 7.98 | 28.4 |

3–4 pounds of the dried product were calcined in $N_2$ for 3 hours at 1000° F.

1329 grams of the calcined product were mixed with 6645 cc of 1 N $NH_4NO_3$ solution for 1 hour at ambient temperature. The mixture was vacuum filtered. The ion exchange procedure was repeated and the final filter cake was dried at 250° F. The sodium content of the final product was less than 0.05% wt.

EXAMPLES 3–6

Using the catalysts of Examples 1 and 2, toluene was alkylated with ethylene. Runs were made at atmospheric pressure over approximately 20 hour periods. The catalysts were diluted with 3 volumes of low surface area quartz chips. Analysis of samples were taken during the first and last hour of each run as indicated by the ranges in the hereinafter tabulated data. The reaction conditions and results obtained are shown in Table III below.

TABLE III

A. Catalyst of Example 1 ($SiO_2/Al_2O_3$ = 1600/1)

| Ex. | Temp °C | WHSV Tol. $C_2H_4$ | CONVERSION, % Toluene | CONVERSION, % $C_2H_4$ | % Para in Ethyl-Toluene | Para Ethyl-Toluene | Meta Ethyl-Toluene | Ortho Ethyl-Toluene | Light* Gases | Other** Aromatics |
|---|---|---|---|---|---|---|---|---|---|---|
| 3 | 350 | 3.5 / .24 | 17.1–12 | 70–54 | 31–33 | 30.1–32.2 | 64.7–64.5 | 1.9–1.3 | .2 | 3.1–1.9 |
| 4 | 400 | 3.5 / .24 | 20.4–17.4 | 86–78 | 29–30 | 28.3–29.9 | 66.6–66.7 | 4.2–3.1 | .4–.1 | .5–.2 |

B. Catalyst of Example 2 ($SiO_2/Al_2O_3$ = 70/1)

| Ex. | Temp °C | WHSV Tol. $C_2H_4$ | CONVERSION, % Toluene | CONVERSION, % $C_2H_4$ | % Para in Ethyl-Toluene | Para Ethyl-Toluene | Meta Ethyl-Toluene | Ortho Ethyl-Toluene | Light* Gases | Other** Aromatics |
|---|---|---|---|---|---|---|---|---|---|---|
| 5 | 350 | 6.9 / .5 | 20.4–19.4 | 93–96 | 27 | 23.8–24.1 | 53.9–55.1 | 11.1–9.9 | .6–1.4 | 10.6–9.5 |
| 6 | 400 | 6.9 / .5 | 19.6–19.7 | 91–98 | 27 | 19.8–21.9 | 43.1–48.3 | 10.4–11.2 | 4.4–2.1 | 22.3–16.5 |

*Light gases are composed of methane, ethane, propane, propylene, $C_4$ paraffins and $C_4$ olefins.
**Other aromatics include benzene, ethylbenzene, xylenes and diethylbenzene.

It will be seen from the above comparative data that the use of high $SiO_2/Al_2O_3$ ZSM-5 catalyst, typified by the catalyst of Example 1, effected a very substantial reduction in undesired by-product formation.

A comparison of the selectivity to side reaction products is summarized in Table IV below.

TABLE IV

| Temp °C | LIGHT GAS, Selectivity $SiO_2/Al_2O_3$ 70/1 | LIGHT GAS, Selectivity $SiO_2/Al_2O_3$ 1600/1 | Reduction 70/1 1600/1 | OTHER AROMATICS, Selectivity $SiO_2/Al_2O_3$ 70/1 | OTHER AROMATICS, Selectivity $SiO_2/Al_2O_3$ 1600/1 | Reduction |
|---|---|---|---|---|---|---|
| 350° | .6–1.4 | .2 | 3–7 fold | 10.6–9.5 | 3.1–1.9 | 3–5 fold |
| 400° | 4.4–2.1 | .4–.1 | 11–21 fold | 22.3–16.5 | .5–.2 | 45–83 fold |

It will be evident that at a reaction temperature of 350° C., 3–7 fold reductions in undesired by-products were observed using the zeolite catalyst of high $SiO_2/Al_2O_3$ ratio and that at 400° C. substantially higher by-product reductions of 11–21 fold for light gas formation and 45–83 fold for other aromatics production were observed.

EXAMPLES 7–9

In a manner similar to that described in Examples 3–6 utilizing the catalysts described in Examples 1 and 2, alkylation of ethylbenzene with ethylene was effected. The conditions of reaction and analytical results are summarized in Table V below.

TABLE V

A. Catalyst of Example 1 (SiO$_2$/Al$_2$O$_3$ = 1600/1)

| Ex. | Temp °C | Run Time Hrs. | WHSV Ethyl-Benzene C$_2$H$_4$ | CONVERSION, % Ethyl-Benzene | C$_2$H$_4$ | SELECTIVITY TO PRODUCTS, wt. % | | | |
|---|---|---|---|---|---|---|---|---|---|
| | | | | | | % Para in Diethyl-Benzene | Diethyl-Benzene | Light Gases | Other Aromatics |
| 7 | 350 | 22 | 7.2 / .55 | 15.5–5.6$^{(a)}$ | 27–10 | 36.9–51.1 | 86.1–82.0 | .4–.8 | 13.5–17.2 |

B. Catalyst of Example 2 (SiO$_2$/Al$_2$O$_3$ = 70/1)

| Ex. | Temp °C | Run Time Hrs. | WHSV Ethyl-Benzene C$_2$H$_4$ | CONVERSION, % Ethyl-Benzene | C$_2$H$_4$ | SELECTIVITY TO PRODUCTS, wt. % | | | |
|---|---|---|---|---|---|---|---|---|---|
| | | | | | | % Para in Diethyl-Benzene | Diethyl-Benzene | Light Gases | Other Aromatics |
| 8 | 350 | 24 | 7.1 / .47 | 53.3–54.2$^{(a)}$ | 68–65 | 28.9–29.2 | 53.8–52.7 | 5.8–6.1 | 40.4–41.2 |
| 9 | 250 | 20 | 7.2 / .48 | 20.3–4.5$^{(a)}$ | 86–3.4 | 35.5–51.1 | 77.5–71.9 | 4.6–2.7 | 17.9–25.4 |

$^{(a)}$Ranges show results for the first and last hour of the run for the time period shown.

It will be seen from the above data that selectivity to the desired diethylbenzene product was substantially greater utilizing the catalyst of higher silica/alumina ratio (1600/1) and that formation of by-product gases and other aromatic compounds was relatively low.

The catalyst of lower silica/alumina ratio (70/1) was much more active as indicated by the high conversion of ethylbenzene at 350° C. Moreover, even when the temperature was lowered to 250° C. to reduce conversion, relatively large amounts of by-products were produced as compared with those obtained utilizing the catalyst of higher silica/alumina ratio.

I claim:

1. Process for effecting ethylation of a mono alkyl benzene wherein the alkyl substituent contains 1 to 2 carbon atoms to yield a mixture of ethyl toluene or diethylbenzene isomers with minimal undesired by-product formation which comprises contacting said mono alkyl benzene with an ethylating agent, under conversion conditions, including a temperature between about 250° C. and about 600° C., a pressure between about 0.1 and about 100 atmospheres, utilizing a feed weight hourly space velocity between about 0.1 and about 1000 and a molar feed ratio of toluene/ethylating agent between about 1 and about 10, in the presence of a catalyst comprising a crystalline aluminosilicate zeolite characterized by a constraint index within the approximate range of 1 to 12 and a silica to alumina ratio greater than about 500.

2. The process of claim 1 wherein said mono alkyl benzene is toluene.

3. The process of claim 1 wherein said mono alkyl benzene is ethylbenzene.

4. The process of claim 1 wherein said ethylating agent is ethylene, ethyl alcohol, ethyl halide, diethyl ether, ethyl mercaptan or diethyl sulfide.

5. The process of claim 1 wherein said crystalline aluminosilicate zeolite is ZSM-5.

6. The process of claim 5 wherein said ethylating agent is ethylene.

7. The process of claim 1 wherein said crystalline aluminosilicate zeolite is admixed with a diluent or a binder therefor.

8. The process of claim 5 wherein said ZSM-5 is admixed with a diluent or a binder therefor.

9. The process of claim 1 wherein said crystalline aluminosilicate zeolite is characterized by a silica to alumina ratio greater than about 500 but not exceeding about 2000.

10. The process of claim 9 wherein said crystalline aluminosilicate zeolite is ZSM-5.

11. The process of claim 1 wherein said crystalline aluminosilicate zeolite is characterized by a silica to alumina ratio greater than about 1000 but not exceeding about 2000.

12. The process of claim 11 wherein said crystalline aluminosilicate zeolite is ZSM-5.

* * * * *

UNITED STATES PATENT AND TRADEMARK OFFICE
CERTIFICATE OF CORRECTION

PATENT NO. : 4,104,319
DATED : August 1, 1978
INVENTOR(S) : Warren W. Kaeding

It is certified that error appears in the above-identified patent and that said Letters Patent are hereby corrected as shown below:

In Column 1, line 13, "2,904,679" should read -- 2,904,697--.

In Column 2, line 53, "usually" should read -- unusually --.

In Column 2, line 56, "catalyst" should read -- catalytic --.

Signed and Sealed this

Sixth Day of March 1979

[SEAL]

Attest:

RUTH C. MASON
Attesting Officer

DONALD W. BANNER
Commissioner of Patents and Trademarks